United States Patent
Cook

(10) Patent No.: US 8,099,159 B2
(45) Date of Patent: Jan. 17, 2012

(54) METHODS AND DEVICES FOR ANALYZING AND COMPARING PHYSIOLOGICAL PARAMETER MEASUREMENTS

(75) Inventor: Vaughn Cook, Orem, UT (US)

(73) Assignee: Zyto Corp., Orem, UT (US)

( * ) Notice: Subject to any disclaimer, the term of this patent is extended or adjusted under 35 U.S.C. 154(b) by 6 days.

(21) Appl. No.: 11/521,417

(22) Filed: Sep. 13, 2006

(65) Prior Publication Data

US 2007/0066874 A1 Mar. 22, 2007

Related U.S. Application Data

(60) Provisional application No. 60/717,538, filed on Sep. 14, 2005.

(51) Int. Cl.
*A61B 5/05* (2006.01)
(52) U.S. Cl. .......................... 600/547; 600/26
(58) Field of Classification Search .................. 600/546, 600/547
See application file for complete search history.

(56) References Cited

U.S. PATENT DOCUMENTS

| | | | |
|---|---|---|---|
| 4,683,891 A * | 8/1987 | Cornellier et al. | 600/301 |
| 5,676,138 A | 10/1997 | Zawilinski | |
| 5,741,217 A | 4/1998 | Gero | |
| 5,771,261 A | 6/1998 | Anbar | |
| 6,325,763 B1 * | 12/2001 | Pfeiffer et al. | 600/549 |
| 6,527,700 B1 * | 3/2003 | Manico et al. | 600/26 |
| 6,743,182 B2 | 6/2004 | Miller et al. | |
| 6,837,615 B2 * | 1/2005 | Newman | 374/45 |
| 2003/0236451 A1 | 12/2003 | El-Nokaly et al. | |
| 2004/0143170 A1 * | 7/2004 | DuRousseau | 600/300 |
| 2005/0154264 A1 | 7/2005 | Lecompte et al. | |
| 2007/0249914 A1 * | 10/2007 | Cacioppo et al. | 600/300 |

* cited by examiner

*Primary Examiner* — Max Hindenburg
*Assistant Examiner* — Renee Danega
(74) *Attorney, Agent, or Firm* — Thorpe North & Western LLP

(57) ABSTRACT

Methods and devices that are capable of measuring physiological parameters of at least two contact points and determining whether the measured parameters reflect favorable or unfavorable physiological responses are disclosed herein. Specifically, the present invention encompasses a method that can non-invasively monitor physiological parameters of at least two contact points before and after a stimulus is applied to a subject and compare the measured parameters to determine whether the physiological state of the subject is favorable or unfavorable.

20 Claims, 3 Drawing Sheets

METHODS AND DEVICES FOR ANALYZING AND COMPARING PHYSIOLOGICAL PARAMETER MEASUREMENTS

Priority of U.S. Provisional patent application Ser. No. 60/717,538 filed on Sep. 14, 2005 is claimed.

FIELD OF THE INVENTION

The present invention relates generally to methods and devices for measuring and evaluating physiological parameters of a living subject.

BACKGROUND OF THE INVENTION

Many have studied the effects of stress and other stimuli on the human body for years. Most refer to stress as a state of mental, emotional, or other psychological strain placed upon one's body. In reality, stress can be any substance or occurrence that places an undue tension or strain on one's physiological and psychological state. A simplistic example is a body's response to the common cold. As a person is exposed to and contracts the common cold virus, the virus will multiply and challenge the body's normal functions by placing an undue stress upon the body. Once the virus is eliminated, the body may return once again to its steady state or normal state. Similarly, emotional disturbances can lead to serious stress responses, often greater than physiological ones. There have been many who have developed methods and devices for analyzing the affects of stress on the human body. Specifically, most have focused on the affects of mental strains or stresses, however, others have focused specifically on physiological stresses.

Around 1950, Dr. Voll, a German doctor studied the electrical properties of acupuncture points and how these properties change as a reflection of stress on the body. Dr. Voll believed that the body responds in a measurable way to stresses that are momentarily placed in proximity to the body. In particular, acupuncture points are situated along acupuncture meridians within a subject's body. The meridians are energetic pathways that traverse along a subject's body. It is believed that acupuncture points relate to various organs and body systems and are more electrically sensitive than surrounding tissue. Measuring the activity around the acupuncture points can help predict whether problems are occurring or will occur within a subject and possibly which bodily organs will be affected.

Other methods and devices for measuring physiological parameters of individuals have been utilized for many years. For example, Galvanic Skin Response (GSR) devices, also known as electrodermal response (EDR), have been used to obtain biofeedback from individuals. Specifically, GSR measures the electrical resistance of the skin and interprets the measurements as an image of activity in certain parts of the body, i.e. biofeedback. Those who have studied human galvanic skin responses believe the more relaxed a person is, the dryer the person's skin will be, thus the higher the skin's electrical resistance will be. When a person is under stress the hand sweats and the resistance goes down. This process has been commonly used in psychophysiology experiments to infer the emotional state of a subject and has also been used in lie detectors, i.e. polygraph devices.

Other known devices have been devised to test specific physiological parameters of a person, such as electroencephalogram (EEG) machines. The EEG machines have been designed to monitor the brain wave activity of a patient. Additionally, some devices measure skin temperature which can be helpful in detecting certain circulatory disorders. Another machine commonly used is an electromyogram (EMG) machines which measures muscle tension in a living subject. Other devices have been employed to monitor heart rate and blood pressure, both of which change in response to stress, arrhythmia and hypertension. As previously mentioned, a lot of emphasis has been placed on monitoring anxiety states of people. These measurements can be adapted in lie detector devices to determine whether a person is telling the truth.

These previous devices have attempted to measure specific physiological parameters but have been met with varying degrees of success. One major down fall is the devices are tailored for measuring a specific physiological parameter. Yet, they offer no real solution for evaluating the physiological measurements or patterns and how it affects a person. For example, most methods and devices are not diverse in its measurements and teach measuring only a specific location for measuring the parameters, i.e. the face. Others believe obtaining biofeedback data can help you train body to over come certain disabilities, i.e. mind over matter.

As such, devices and methods that measure and evaluate stress responses in a living subject thereby providing the subject with beneficial information continues to be sought through ongoing research and development efforts.

SUMMARY OF THE INVENTION

Accordingly, the present invention is drawn towards methods that evaluate stress response patterns in living subjects. Such a method may include locating at least two contact points on an area of skin of the subject and measuring physiological parameters of the at least two contact points to determine a baseline reading. The baseline reading is typically a real-time dynamic baseline reading indicating the physiological state of the at least two contact points at any given moment. Once the baseline reading is determined, an external stimulus can be applied to the subject. Any stimulus may be applied to a subject but non-limiting examples can be verbal statements and images, electroshock, thermal, pressure, emotional activity, odor, subliminal, verbal and visual stimulus. After applying at least one external stimulus the physiological parameters of the at least two contact points can be re-measured to determine a stress response. Subsequently, the dynamic baseline reading and the stress response can be compared to determine whether the stress response is indicative of either a symmetrical stress response pattern or an asymmetrical stress response pattern. Once the stress response pattern is determined, the pattern can be assigned to a specific category. Specifically, the symmetrical stress response pattern can be assigned to a category that is a favorable stress response and the asymmetric stress response pattern can be assigned to a category that is an unfavorable stress response.

In one embodiment, the present invention encompasses a method of analyzing stress measurements of a living subject. Such a method may include taking at least two physiological measurements before and after an external stimulus is applied to the subject, comparing the physiological measurements taken before and after the application of the stimulus and determining whether the physiological measurements diverge, converge or remain unchanged with respect to each other, thereby indicating whether the physiological measurement responses are favorable or unfavorable to the subject.

In an alternative embodiment, the present invention also contemplates a method of determining the physiological state of a living subject, which may comprise measuring the physiological responses of at least two contact points on a subject before and after an external stimulus is applied to the subject and comparing the measured physiological responses to determine whether the physiological responses reflect a favorable or an unfavorable physiological state of the subject. If the physiological state is unfavorable, a trained person skilled in the art would be able to analyze the results and suggest options for returning the physiological state to a more favorable status.

The present invention also contemplates a device for measuring physiological parameters of a living subject. Specifically, such a device can be a sensor device configured for measuring physiological parameters of at least two contact points of skin of a living subject. The device may include a measuring element configured to contact at least two contact points on a subject and to measure a sequence of physiological parameters of these contact points. Additionally, a computing source having an algorithm for determining whether the measurements are a favorable stress response based on a positive sequence or an unfavorable stress response based on a negative sequence. Further, at least one sensor may be coupled to the measuring element for conveying the physiological parameter measurements to a computing source.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawing and claims, or may be learned by the practice of the invention.

Figure 1:
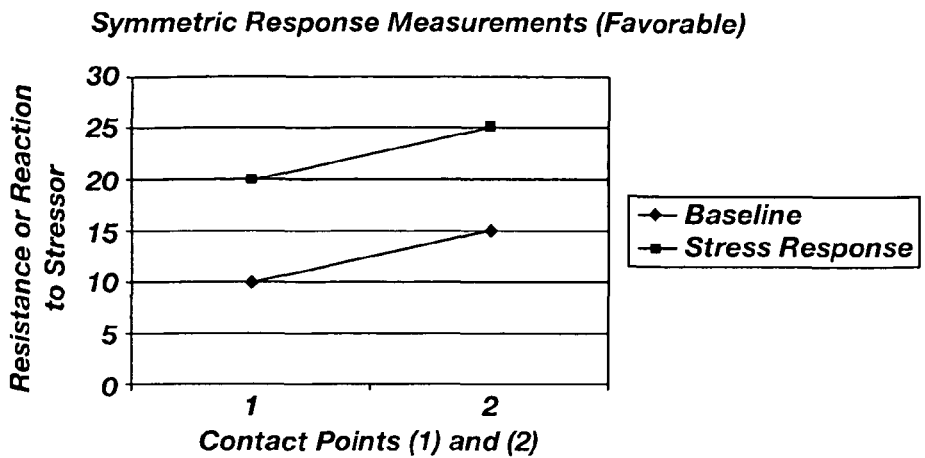
FIG. 1 is a graphic representation of a symmetric response in accordance with one embodiment of the present invention.

The drawings will be described further in connection with the following detailed description. Further, the numerical values used to graph the representation of particular responses is not considered to be an accurate representation of values conducted tests on a subject but are merely used to demonstrate numerically how particular responses are determined.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

DEFINITIONS

In describing and claiming the present invention, the following terminology will be used.

The singular forms "a," "an," and "the" include plural referents unless the context clearly dictates otherwise. Thus, for example, reference to "a stressor" includes reference to one or more of such stressors, and reference to "a parameter" includes reference to one or more of such parameters.

As used herein, "stress" refers to any reaction that occurs in the body as a result of internal and external stimuli. Generally, the term stress is not only inclusive of emotional nervousness but can also be any physical reaction on the body.

As used herein, "stressor" refers to any stimulus that causes a reaction in a living subject. In accordance with some embodiments of the present invention, a stressor is referred to as an external stimulus, i.e. electrostatic shock.

As used herein, "stress response" refers to a subject's reaction after a stimulus or stressor has been applied to the subject. According, to some aspects of the present invention the stress responses can be measured in microsiemens ($\mu S$) or degrees Fahrenheit. The stress response can be categorized as either favorable or unfavorable to the subject.

As used herein, "biofeedback" refers to a technique or process that uses instrumentation to give a person immediate and constant feedback of change in his/her bodily function of which he/she is usually unaware. For example, a biofeedback process can measure bodily functions, like breathing, heart rate, blood pressure, skin temperature, and muscle tension.

As used herein, "physiological parameter" relates to one of many variables of measuring or evaluating bodily function of a subject. Such a variable can have a measure that is indicative of a quantity or function that cannot itself be precisely determined by direct methods, for example, blood pressure and pulse rate are parameters of cardiovascular function.

As used herein, "baseline" refers to information or a value that represents a normal steady state level, or an initial level, of a measurable quantity, used for comparison with values representing response to stimuli. The measurements of the baseline and response values refer to the same individual or system. In accordance with the present invention the baseline is generally a dynamic baseline reading.

As used herein, "symmetric" refers to values of common measurements that on a graphic scale move in the same orientation or move closer together. A symmetric response refers to a substantially balanced physiological parameter.

As used herein, "asymmetric" refers to non-symmetrical or unbalanced responses. In other words, the values of common measurements on a graphic scale will move farther apart from each other.

Any numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a response range of 0.5 to 400 should be interpreted to include not only the explicitly recited response limits of 0.5 and 400, but also to include individual responses within that range, such as 0.5, 0.7, 1.0, 5.2, 8.4, 11.6, 14.2, 100, 200, 300, and sub-ranges such as 0.5-2.5, 4.8-7.2, 6-14.9, 55, 85, 100-200, 117, 175, 200-300, 225, 250, and 300-400, etc. This interpretation should apply regardless of the breadth of the range or the characteristic being described.

THE INVENTION

The present invention encompasses methods and devices that are capable of measuring physiological parameters of at least two contact points and determining whether the measured responses of those parameters reflect favorable or unfavorable physiological responses. Specifically, the present invention contemplates a method that may include locating at least two contact points on a subject and measuring the physiological parameters of said subject to obtain a baseline response reading. Once the baseline reading is obtained an external stimulus may be applied to the subject. Re-measuring the same contact points can then be performed to determine the magnitude of response to the stimulus and comparing the re-measured parameters with the baseline reading to determine whether the response pattern is favorable or unfavorable to the subject.

As noted in the background section, many have studied and designed devices for measuring parameters of the body. Specifically, there are those that believe physiological parameters of acupuncture points are the only contact points that provide viable biofeedback. However, it has recently been discovered by the inventor of the present invention there are various contact points or areas which can be sampled and evaluated which are capable of providing an individual important personal biofeedback. Accordingly, the contact points can be acupuncture points found anywhere on a subject's body. Alternatively, the contact points may be any dermal area located on the subject's forearms, thighs, calves, shoulders, back, neck, head, and hands, to name a few. In one exemplary embodiment the area of contact can be the hand. The present invention requires at least two points of contact but can use multiple contact points. Specifically, the present invention contemplates locating at least one contact point found on each finger of a hand and measuring all fingers to obtain the physiological baseline reading and stress response.

The physiological parameters most often measured are variables that can provide some form of biological feedback to the subject. Particularly, the parameters are variables that are indicative of a quantity or function that cannot itself be precisely determined by direct measurement methods, for example, blood pressure and pulse rate are parameters of cardiovascular function. Specifically, there is no true method or device that can measure bodily functions, i.e. the cardiovascular function, apart from measuring parameters of that system, i.e. blood pressure. According to one aspect of the present invention, the physiological parameters may include galvanic skin response (GSR), skin temperature, moisture content, blood pressure, respiratory movement, muscle tension and eye movements. Other physiological parameters or signals that may be measured which are not specifically referenced herein are blood oxygen content and brain waves. In one preferred embodiment, the physiological parameter can be a subject's galvanic skin response function.

The initial step in the above mentioned method is to non-invasively measure the physiological parameters of the contact points thereby obtaining and establishing a personal baseline reading. According to some aspects, the baseline is a series of values that represent a normal steady state, or an initial state of an individual which can be used for comparing values representing stress responses after applying a stimulus. Notably, every individual is unique, thus baselines obtained will vary with each individual. In one embodiment the method contemplates taking multiple cutaneous physiological measurements in tandem at each designated contact point. The initial step of measuring each contact point may be repeated multiple times prior to applying any type of a stimulus to the subject, such that a more accurate physiological baseline can be obtained. In one embodiment of the present invention the baseline is a real-time dynamic baseline reading. Once a reliable personal baseline has been established at least one stressor and preferably multiple stressors may be applied to the subject. Notably, each person functions different and the concentration or amount of stimulus applied may vary for each individual.

A stressor or also referred to herein as a stimulus can help provide valuable and measurable data to the subject. The stimulus can be an internal stressor and more preferably an external stressor. Suitable internal stressors can be any substance that produces some form of a physiological change within the subject. For example, an internal stimulus can be used, such as a drug cause physiological changes from within the subject's body. Preferably, an external stimulus may be used to gauge possible changes in a subject's established baseline. Multiple successive stressors are typically applied to the subject and the baseline can be tracked pursuant to application of each stressor. The stressors can be constant or varying in strength depending on the resistance and the specific characteristics of the subject. Suitable external stressors may include electroshock, thermal, pressure, emotional, odor, subliminal, verbal and visual stimulus. In a preferred embodiment the stressor can be an electromagnetic wave used to measure the galvanic skin responses of an individual.

The response to external stimulus can be indicative of the certain health conditions of the subject. For example, galvanic skin responses can indicate whether the subject is in a relaxed state or stressed state. As noted above, galvanic skin responses are changes in the electrical properties of the subject's skin. The change in electrical properties occurs due to a stressor and the individual's physiological state. The human skin can conduct small amounts of electricity, thus when a low electrical current is applied to the skin, a change in electric conductance or the resistance of the skin can be measured in $\mu S$. The electrical conductance of human skin is typically categorized as either phasic or tonic conductance. Phasic conductance refers to stimulus related changes in skin conductance. Meaning, the change in electrical skin conductance can be stimulated by any type of stimuli, i.e. temperature, water content, odor, etc. On the other hand, tonic skin conductance refers to electrical skin conductance at a steady state or in the absence of stimuli. By evaluating the change in these two types of skin conductance it is believed that certain measurable values can signify certain physiological states of particular organs or of the subject in general.

Comparing and evaluating the measured parameters can predict the physiological patterns or the stress levels of an individual. In particular the methods recited herein can determine whether stress responses are favorable or unfavorable responses to a person. As previously discussed, the method contemplates testing at least two contact points on an area of skin of a person to determine a physiological baseline. Typically, the baseline reflects the physiological state of the individual at a substantially steady state or in other words in the absence of a stimulus. Once a baseline has been determined, a stimulus is applied to the individual and the same contact points are re-measured and the deviation between the baseline and stress response is calculated. This deviation can be known as a deviation ratio. The numerical values of the deviation ratio may indicate whether the stress responses are favorable or unfavorable responses to a subject. Generally, a positive deviation ratio indicates that the response is symmetric (favorable) and a negative deviation ratio indicates that the response is asymmetric (unfavorable).

Figure 2:
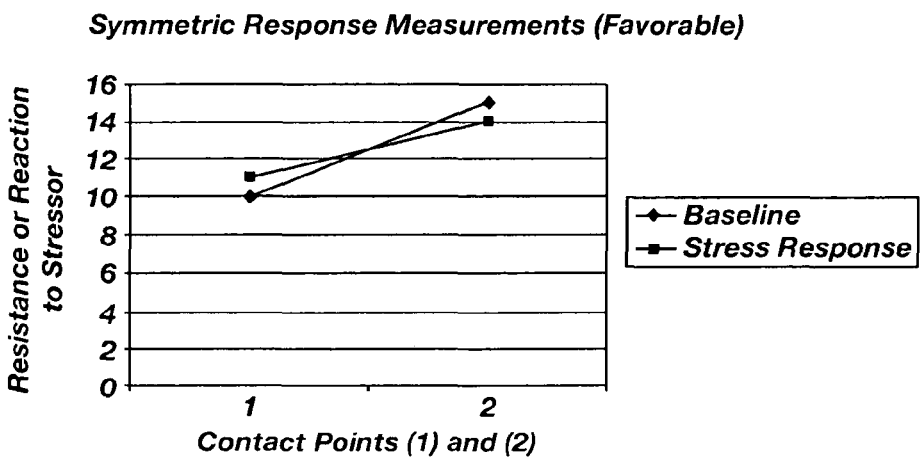
FIG. 2 is another graphic representation of a symmetric response in accordance with another embodiment of the present invention.
Figure 3:
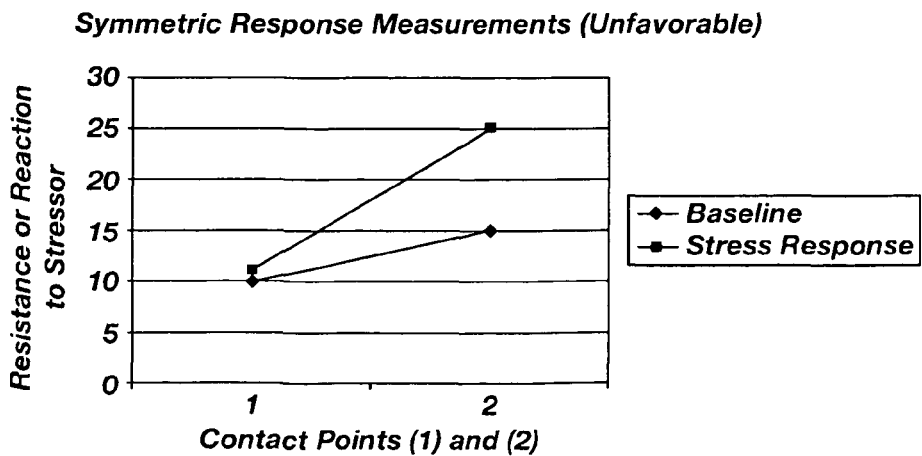
FIG. 3 is a graphic representation of an asymmetric response in accordance with one embodiment of the present invention.

Referring now to FIGS. 1-3, are depicted graphical representations of symmetric and asymmetric responses. In particular, FIG. 1, reveals a GSR baseline and stress response reading for each contact points (1) and (2). The baseline reading indicates that under normal conditions the subject has a GSR reading of about 10 μS and 15 μS for contact points (1) and (2), respectively. After a stimulus is applied, the GSR shifted to 20 and 25, respectively. The shifting of these two successive points on a graphic scale in a substantially same direction and by substantially the same amount, indicates that the responses are symmetric or in other words the deviation ratio is positive. FIG. 2, shows a GSR parameter reading of 10 and 15 μS for contacts points (1) and (2). After the stimulus is applied the response yielded values of 11 and 14 for contact points (1) and (2). The numerical value of each contact point move closer towards one another, thereby indicating another symmetric response or alternatively, a positive deviation ratio response. In contrast, FIG. 3 shows baseline values for contact points (1) and (2) as 10 and 15 μS. Subsequent to the application of an external stimulus, the individual subconsciously responds with values of 11 and 25 μS for contact points (1) and (2), respectively. These two successive points move away from each other on the graphic scale, indicating an asymmetric response or a negative deviation value.

Once the responses have been measured and the deviation values have been calculated by an algorithm, the responses can be categorized as being either favorable or unfavorable to a subject. A favorable stress response is indicative of measured values that either converge toward each other or remain substantially unchanged, i.e. symmetric. An unfavorable stress response is indicative of measured values that diverge from each other, i.e. asymmetric. Further a favorable response can imply that the individual is substantially healthy. While an unfavorable response can suggest or predict that the individual will become unhealthy and may require drugs or nutritional supplements to improve the unhealthy condition. At the least, an unfavorable response may indicate that the person should undergo more treatments or evaluations to determine why the responses are unfavorable.

If an individual receives an unfavorable response, vitamin supplements may be consumed by the individual to combat the stressors that may be affecting the body. For example, if a subject has contracted the common cold virus and after evaluating his/her physiological state, then the individual may consume a supplemental material that can aid in the elimination and combating of the virus. Further, the contact points of the individual may be retested to determine whether the supplement is helping to obtain a more favorable stress response and whether the supplemental dosage is proper. In this manner a person may be able to eliminate those supplements that lack the beneficial results needed.

Figure 4:
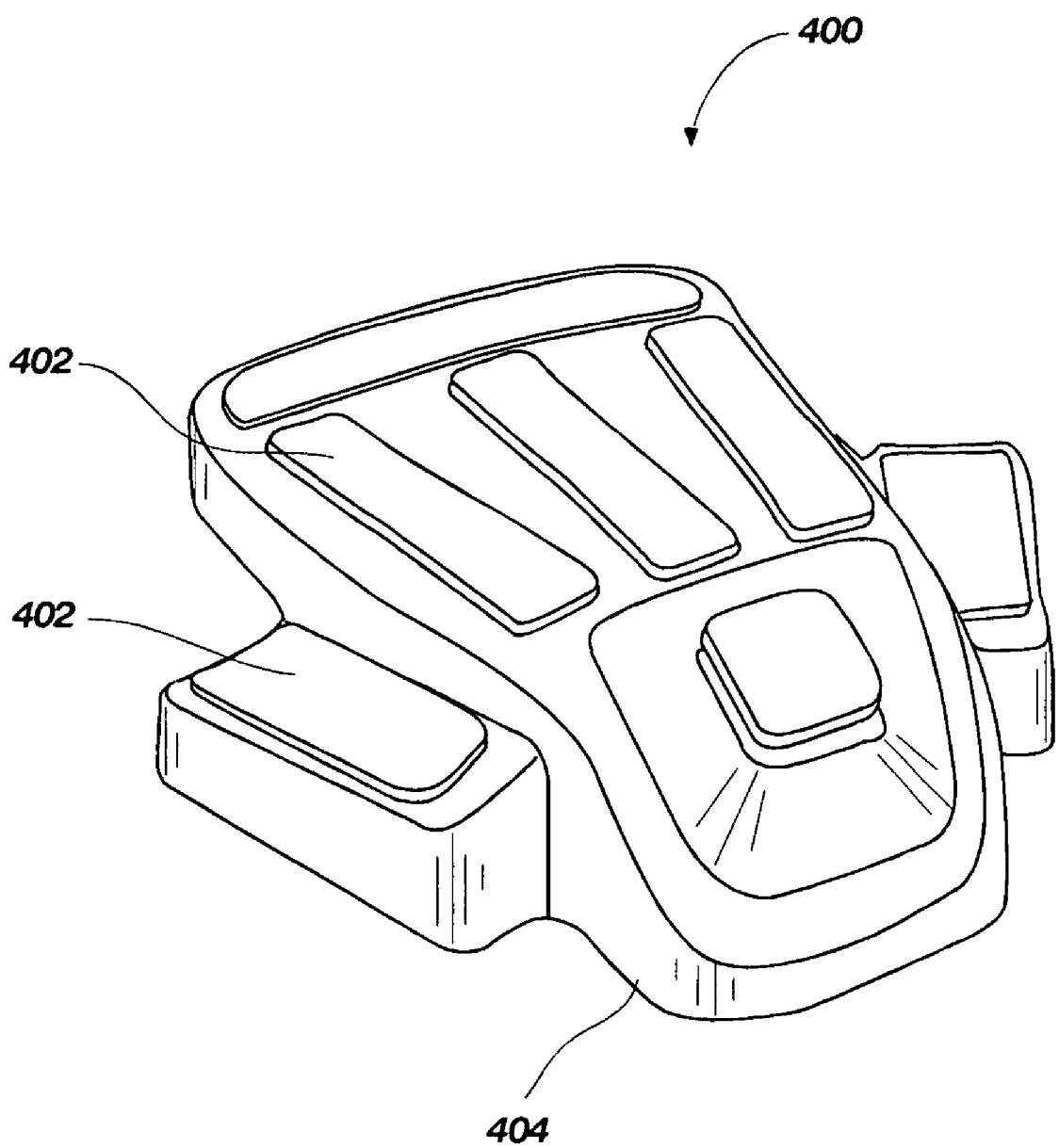
FIG. 4 is a schematic drawing of a hand cradle having measuring elements in accordance with one embodiment of the present invention.

The present invention also contemplates a device or a sensor device used to evaluate physiological stress patterns or the physiological state of the individual. Such a device can generally measure the physiological parameters of at least two cutaneous contact points of a living subject. The device may include a measuring element which has been configured to contact the at least two contact points and to measure a sequence of physiological parameters of the subject. The measuring element may be any substrate that can contact the dermal layer or may be coupled to a plurality of sensor devices. For example, FIG. 4 illustrates a hand cradle 400 having a plurality of measuring elements 402 coupled to a rigid substrate member 404 and each measuring element can be coupled to at least one sensor (not shown) configured to test the galvanic skin responses in the individual's hand can be employed. In this example the measuring element can be comprised of any material that can conduct energy and the substrate member may be any solid or rigid material such as plastic or metal. A more complex device may include multiple measuring elements having a plurality of sensors coupled thereto and configured to monitor and measure the variances in the phasic and tonic skin conductance properties. In other embodiments, the device can be configured to monitor and test other physiological parameters as described herein. For example, the measuring element may be coupled to at least one thermometer capable of detecting and measuring minute changes in skin temperature. In an alternative embodiment the measuring element may be coupled to other sensors configured to measure or monitor changes in various physiological parameters such as respiratory air flow, respiratory excursions, muscle movements, heart pulses, blood pressure and blood oxygen content levels.

Furthermore, the sensors may also be coupled to a computing source and configured for conveying physiological parameter measurements from the measuring element to the computer source. Typically, the sensor is coupled to the computing source via direct wire or telemetry, however, the sensor may be coupled to the computing source via other data communication means. Various telemetry systems may be used such as wireless transmission systems. Suitable wireless systems may include standard of IEEE 802.11, IEEE 802.15, Bluetooth, Ultra Wide Band, Radio Frequency or other mesh networks, such as BAN, WPAN, and WLAN.

Generally, the computing source has a user interface for operating and receiving information from the measuring elements. In one embodiment of the present invention the computing source may include an algorithm for determining whether the physiological measurements are favorable or unfavorable stress responses based upon a positive or negative sequence, respectively. Typically, the favorable and unfavorable stress responses are converted into a signature and are compared to pre-designated signatures stored in a library included with the computer source.

In one embodiment, the computing source may include a library having pre-designated signatures representing certain physiological parameter responses. Generally, the algorithm associated with the present device can be configured to compare the physiological responses with the pre-designated signatures thereby predicting whether the responses are favorable or unfavorable and possibly provide remedial feedback to the subject. Optionally, the remedial feedback may provide specific therapeutic remedies or nutritional supplements that may be taken in order to shift the responses into a favorable category.

Figure 5:
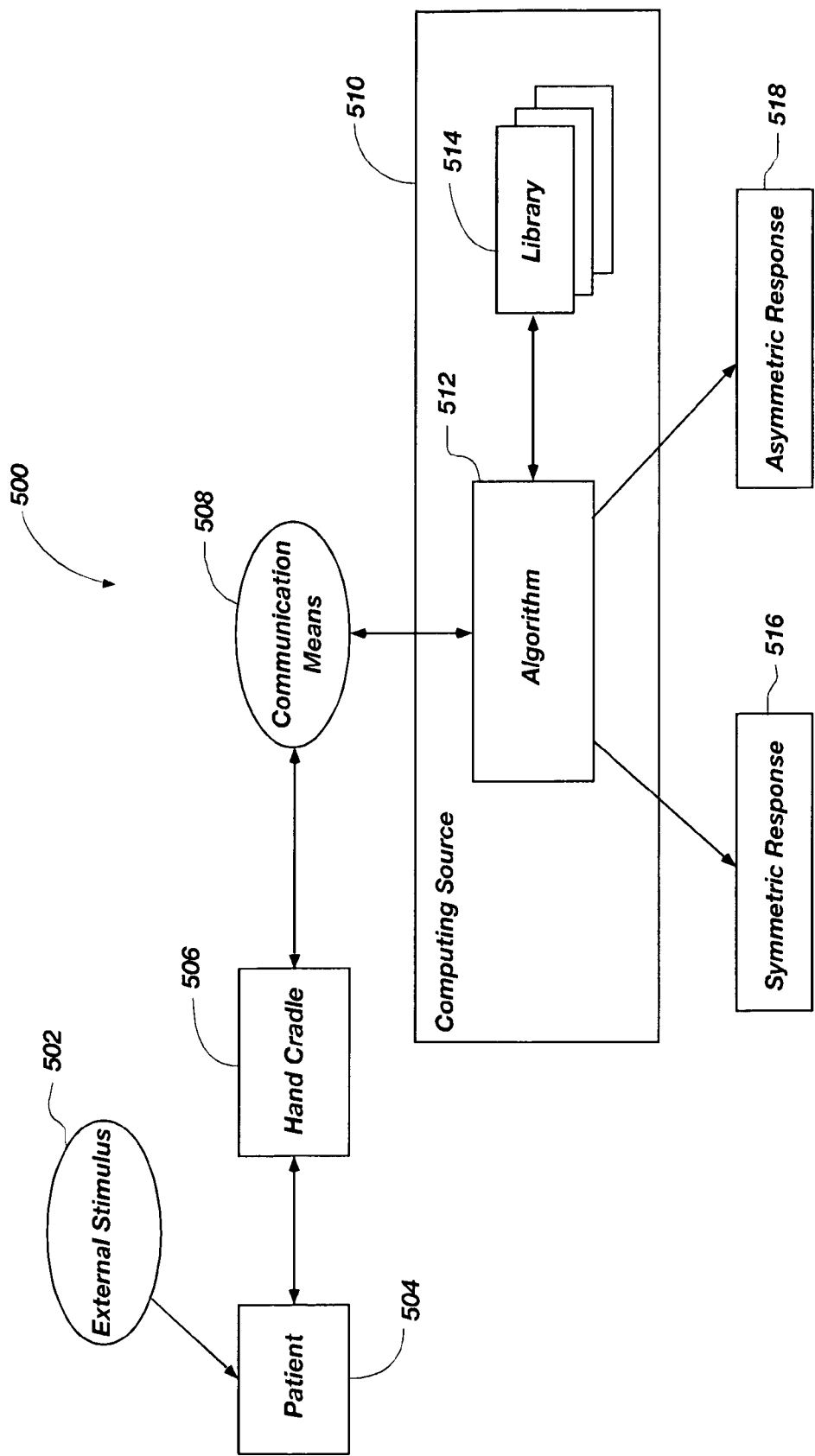
FIG. 5 illustrates a block diagram depicting a system for evaluating stress response patterns in a subject.

FIG. 5 depicts a block diagram of system 500 that can evaluate stress response patterns in a patient. The system may include a patient 504 to be tested, a hand cradle 506 and a computing source 510. As previously described herein, the hand cradle can monitor and test galvanic skin responses, physiological parameters, of the patient at a normal steady state to obtain a baseline with the aid of sensors and measuring elements (not shown). Once a baseline response is established, an external stimulus 502 can be applied to the patient. The handle cradle measures the patient's galvanic skin response subsequent to the applied stimulus. A communications means 508, such as direct wire or wireless communication means, can convey the responses and data to the computing source. The computing source typically contains an algorithm 512 and a library 514. The algorithm can be configured to process the galvanic skin responses with the baseline reading to determine whether the physiological measurements are favorable or unfavorable stress responses. Typically, the favorable and unfavorable stress responses are converted by the algorithm into a signature and are compared to pre-designated signatures stored in the library included with the computer source. Once compared, the responses may be assigned a category of either symmetric (favorable) response 516 or asymmetric (unfavorable) response 518.

These responses may be manifested to the patient or a certified operator via an output device, such as a monitor, thereby the providing the patient with the information such that appropriate therapy actions may be taken if needed.

It is to be understood that the above-described arrangements are only illustrative of the application of the principles of the present invention. Numerous modifications and alternative arrangements may be devised by those skilled in the art without departing from the spirit and scope of the present invention. Thus, while the present invention has been fully described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

EXAMPLE

A human subject manifesting classic symptoms of a common cold can be tested with a number of stressors associated with the common cold. The test can include stressors of various viruses and alternative therapeutic substances (drugs, nutritional supplements, etc.) known to have an affect in either fighting viruses, treating symptoms of the common cold, or generally supporting the immune system. By monitoring the subject's physiological parameter before and after an applied stimulus, a certified operator may be able to infer cause and effect based upon the stress responses and may at least be able to narrow the field of possibilities for further investigation. If, however, virus samples are used as stressors, those that correlate with asymmetrical deviation responses will be suspect as the cause. Subsequent testing with therapeutic substances as stressors, i.e. those that correlate with asymmetrical deviation response, will be weighed more heavily in clinical decisions regarding therapy.

What is claimed is:

1. A method of evaluating stress response patterns in a living subject, comprising the steps of:
    locating at least two contact points on an area of skin of the subject;
    measuring physiological parameters of the at least two contact points to determine individual respective baseline readings of each of the at least two contact points;
    calculating a baseline response differential between the individual baseline readings of the at least two contact points;
    applying an external stimulus to the subject;
    re-measuring the physiological parameters of the at least two contact points after the applied external stimulus to determine individual respective stress response readings of each of the at least two contact points;
    calculating a post-stimulus response differential between the individual post-stimulus readings of the at least two contact points;
    comparing the baseline response differential against the post-stimulus response differential to identify a biological preference to the external stimulus by determining one of a symmetrical stress response pattern and an asymmetrical stress response pattern in the response differentials.

2. The method of claim 1, wherein the at least two contact points are located on an area of skin on a hand of the subject.

3. The method of claim 1, wherein the physiological parameters are selected from a group consisting of galvanic skin response (GSR), temperature, moisture content, and pressure parameters.

4. The method of claim 1, wherein the baseline readings are a real-time dynamic baseline reading.

5. The method of claim 1, wherein the step of measuring is accomplished by a hand cradle device.

6. The method of claim 1, wherein the symmetrical stress response pattern is indicative of response differentials that either converge toward each other or remain substantially unchanged.

7. The method of claim 1, wherein the asymmetrical stress response pattern is indicative of response differentials that diverge from each other.

8. The method of claim 1, wherein the external stimulus is selected from a group consisting of electroshock, thermal, pressure, emotional, odor, subliminal, verbal and visual stimulus.

9. The method of claim 1, wherein the step of comparing is accomplished by a computer source including an algorithm configured to determine one of a symmetrical stress response pattern and an asymmetrical stress response pattern to identify a biological preference to the external stimulus.

10. The method of claim 1, wherein the steps of measuring and re-measuring are accomplished by a non-invasive measuring technique.

11. A system for measuring physiological parameters of at least two contact points of skin of a living subject, comprising:
    a measuring element configured to contact the at least two contact points and to measure a sequence of the physiological parameters of the subject, the sequence comprising:
        individual respective baseline readings of each of the at least two contact points before the application of an external stimulus to the living subject; and
        individual respective stress response readings of each of the at least two contact points after the application of the external stimulus to the living subject;
    a computing source having:
        an algorithm for comparing a baseline response differential between the individual baseline readings of the at least two contact points against a post-stimulus response differential between the respective individual stress response readings of the same contact points after the applied external stimulus; and
        an algorithm for determining one of a symmetrical stress response pattern and an asymmetrical stress response pattern between the baseline and post-stimulus response differentials; and
    at least one sensor coupled to the measuring element for conveying the physiological parameter measurements to the computing source.

12. The system of claim 11, wherein the computing source includes a library which stores pre-designated signatures representing certain physiological parameter measurements and an algorithm that compares the measurements with the pre-designated signatures to determine whether the response differentials indicate a favorable response or an unfavorable response.

13. The system of claim 11, wherein the at least one sensor is an electrode configured to measure galvanic skin responses.

14. The system of claim 11, wherein the sensor is further coupled to the computing source via direct wire or telemetry.

15. The system of claim 14, wherein the telemetry is a wireless transmission of data utilizing the standard of IEEE 802.11, IEEE 802.15, Bluetooth, Ultra Wide Band, Radio Frequency or other mesh networks.

16. The system of claim 11, wherein the measuring element is a hand cradle device having multiple finger contact points.

17. The system of claim 11, wherein the sensor detects changes in GSR, temperature, moisture content and pressure relating to the at least two contact points.

18. A method of analyzing stress measurements of a living subject, comprising:
   taking a physiological measurement from at least two contact points on an area of skin of the subject before and after an external stimulus is applied to the subject;
   calculating a baseline and a post-stimulus response differential between the at least two contact points taken before and after the application of the stimulus, respectively; and
   determining whether the baseline and post-stimulus response differentials converge or remain substantially unchanged, thereby indicating that the response to the external stimulus is favorable, or whether the baseline and post-stimulus response differential diverge, thereby indicating that the response to the external stimulus is unfavorable.

19. A method of determining the physiological state of a living subject, comprising the steps of:
   measuring the physiological responses of each of at least two contact points on the subject before and after an external stimulus is applied to the subject; and
   comparing baseline and post-stimulus response differentials in the physiological responses between the at least two contact points as measured both before and after the external stimulus, respectively, to determine whether a change in the response differential reflects a favorable or an unfavorable physiological state of the subject.

20. The method of claim 1, further comprising assigning the symmetrical stress response pattern to a category that is a favorable stress response and the asymmetric stress response pattern to a category that is an unfavorable stress response.

* * * * *